US010667558B2

(12) United States Patent
Bessant et al.

(10) Patent No.: US 10,667,558 B2
(45) Date of Patent: Jun. 2, 2020

(54) VAPORIZER FOR AN AEROSOL-GENERATING SYSTEM AND VAPORIZING METHOD

(71) Applicant: Altria Client Services LLC, Richmond, VA (US)

(72) Inventors: Michel Bessant, Neuchatel (CH); Fabien Duc, Neuchatel (CH); Zachary Elliott, Loughborough (GB); Robert Emmett, Neuchatel (CH); Hossein Ostadi, Derby (GB); Shaun Phillips, Peterborough (GB); Bruce Renfrew, Leicester (GB); Eva Saade Latorre, Neuchatel (CH); Saad Ali, Loughborough (GB)

(73) Assignee: ALTRIA CLIENT SERVICES LLC, Redmond, VA (US)

( * ) Notice: Subject to any disclaimer, the term of this patent is extended or adjusted under 35 U.S.C. 154(b) by 121 days.

(21) Appl. No.: 15/825,330

(22) Filed: Nov. 29, 2017

(65) Prior Publication Data

US 2018/0146709 A1    May 31, 2018

Related U.S. Application Data

(63) Continuation of application No. PCT/EP2017/077687, filed on Oct. 27, 2017.

(30) Foreign Application Priority Data

Nov. 29, 2016  (EP) ..................... 16201229

(51) Int. Cl.
*A24F 47/00* (2020.01)
*A61M 11/04* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .................................................. A24F 47/008
See application file for complete search history.

(56) References Cited

U.S. PATENT DOCUMENTS 9,055,617 B2 *  6/2015  Thorens ................... H05B 3/58
9,814,263 B2 * 11/2017  Cochand .............. A61M 11/041
(Continued)

FOREIGN PATENT DOCUMENTS

WO    WO-2014/150552 A1    9/2014
WO    WO-2014/153515 A1    9/2014
(Continued)

OTHER PUBLICATIONS

International Search Report and Written Opinion dated Jan. 4, 2018.
(Continued)

*Primary Examiner* — James Harvey
(74) *Attorney, Agent, or Firm* — Harness, Dickey & Pierce, P.L.C.

(57) ABSTRACT

The vaporizer includes a tube element defining an inner volume for receiving an amount of liquid aerosol-forming substrate, a mesh in the inner volume of the tube element, and a heater outside, the heater including an electrical resistive heater, and the heater is configured to heat the mesh and the received amount of liquid aerosol-forming substrate to a temperature sufficient to volatilize at least a part of the received amount of liquid aerosol-forming substrate.

13 Claims, 4 Drawing Sheets

(51) Int. Cl.
  *H05B 3/44* (2006.01)
  *H05B 3/04* (2006.01)
  *A61M 15/06* (2006.01)
  *H05B 3/06* (2006.01)
  *A61M 16/00* (2006.01)

(52) U.S. Cl.
  CPC ................. *H05B 3/04* (2013.01); *H05B 3/44* (2013.01); *A61M 2016/0024* (2013.01); *A61M 2016/0027* (2013.01); *A61M 2205/3334* (2013.01); *A61M 2205/3633* (2013.01); *A61M 2205/3653* (2013.01); *A61M 2205/50* (2013.01); *H05B 3/06* (2013.01); *H05B 2203/021* (2013.01); *H05B 2203/022* (2013.01)

(56) References Cited

U.S. PATENT DOCUMENTS

| | | | |
|---|---|---|---|
| 10,418,840 B2* | 9/2019 | Elliott | H02J 7/0044 |
| 2014/0283855 A1 | 9/2014 | Hawes et al. | |
| 2016/0120221 A1 | 5/2016 | Mironov et al. | |
| 2016/0329574 A1* | 11/2016 | Ostadi | H01M 8/0206 |
| 2017/0172212 A1* | 6/2017 | Phillips | F04B 19/006 |
| 2018/0070640 A1* | 3/2018 | Bessant | A24F 47/008 |
| 2018/0146709 A1* | 5/2018 | Bessant | A24F 47/008 |
| 2018/0146710 A1* | 5/2018 | Bessant | A24F 47/008 |
| 2018/0146711 A1* | 5/2018 | Mazur | A61M 11/02 |
| 2018/0177222 A1* | 6/2018 | Emmett | A24B 3/14 |
| 2019/0320717 A1* | 10/2019 | Tabasso | A24F 47/008 |

FOREIGN PATENT DOCUMENTS

| | | |
|---|---|---|
| WO | WO-2015/073564 A1 | 5/2015 |
| WO | WO-2017/108394 A1 | 6/2017 |
| WO | WO-2017/108429 A1 | 6/2017 |

OTHER PUBLICATIONS

European Search Report for European Application No. 16201229.8 dated Jun. 23, 2017.

* cited by examiner

Fig. 4B

VAPORIZER FOR AN AEROSOL-GENERATING SYSTEM AND VAPORIZING METHOD

CROSS-REFERENCE TO RELATED APPLICATIONS

This application claims is a continuation of, and claims priority to, International Application No. PCT/EP2017/077687, filed on Oct. 27, 2017, and further claims priority under 35 U.S.C. § 119 to European Patent Application No. 16201229.8, filed on Nov. 29, 2016, the entire contents of each of which are herein incorporated by reference.

BACKGROUND

Example embodiments relate to a vaporizer for an aerosol-generating system and to a vaporizing method for evaporating a liquid aerosol-forming substrate such as handheld aerosol-generating systems, such as electrically operated aerosol-generating systems.

Aerosol-generating systems comprise a liquid storing portion for storing a liquid aerosol-forming substrate and an electrically operated vaporizer having a heater for evaporating the aerosol-forming substrate. An aerosol is generated when the evaporated aerosol-forming substrate condenses in an airflow passing the heater. The liquid aerosol-forming substrate may be dispensed directly onto the heater of the vaporizer. In this case the dispensed liquid tends to cool the heater locally.

SUMMARY

As an undesired consequence, amounts of liquid may drip from low temperature areas of the heater without being vaporized. This issue may be solved by delivering the liquid aerosol-forming substrate to the vaporizer by means of a wick. The wick may be made of a porous wicking material. Such a porous wicking material is capable of retaining the liquid and spreading the liquid on the surface of the heater. These wicks are often enclosed, and heated, by the heater. The heater vaporizes the liquid retained in the wick. A problem often observed in these aerosol generating systems is leakage of liquid from them, which can be inconvenient if they are carried in a pocket of the trousers of an adult vaper.

Hence, it would be desirable to have a vaporizer for an aerosol-generating system and a vaporizing method that provide sufficient vaporization of a liquid aerosol-forming substrate and are capable of avoiding an amount of liquid drips from the heater.

According to an example embodiment, a vaporizer comprises a tube element, a mesh, and a heater. The tube element has an inner volume for receiving an amount of liquid aerosol-forming substrate. The mesh is provided in the inner volume of the tube element. The heater is configured for heating the tube element. The heater is provided outside of the tube element. The tube element is thermally conductive. The heater is configured for heating the mesh and the received amount of liquid aerosol-forming substrate to a temperature sufficient to volatilize at least a part of the received amount of liquid aerosol-forming substrate.

At least one example embodiment provides a vaporizer for an aerosol-generating system. The vaporizer includes a tube element defining an inner volume for receiving an amount of liquid aerosol-forming substrate, a mesh in the inner volume of the tube element, and a heater outside, the heater including an electrical resistive heater, and the heater is configured to heat the mesh and the received amount of liquid aerosol-forming substrate to a temperature sufficient to volatilize at least a part of the received amount of liquid aerosol-forming substrate.

In an example embodiment, the heater is configured to indirectly heat the mesh and the received amount of liquid aerosol-forming substrate by heat conduction via the tube element.

In an example embodiment, the mesh is a metal mesh.

In an example embodiment, the mesh is a rolled mesh.

In an example embodiment, the mesh extends along a longitudinal direction of the tube element.

In an example embodiment, the mesh extends from one end to another end of the tube element.

In an example embodiment, the tube element has an open end.

In an example embodiment, the tube element has a closed end, and the tube element includes a number of micro perforations.

In an example embodiment, the tube element is electrically isolated.

In an example embodiment, the heater is surrounded by a thermal insulation element.

At least one example embodiment provides an aerosol-generating system, including a vaporizer and a dispenser. The vaporizer includes a tube element defining an inner volume for receiving an amount of liquid aerosol-forming substrate, a mesh in the inner volume of the tube element and a heater outside, the heater including an electrical resistive heater, and the heater is configured to heat the mesh and the received amount of liquid aerosol-forming substrate to a temperature sufficient to volatilize at least a part of the received amount of liquid aerosol-forming substrate. The dispenser is configured to supply a selected amount of the liquid aerosol-forming substrate to the inner volume of the tube element of the vaporizer.

At least one example embodiment provides a method for generating an aerosol, the method including delivering an amount of liquid aerosol-forming substrate to an inner volume of a tube element of a vaporizer, thereby wetting a mesh provided in the inner volume of the tube element with at least a part of the delivered amount of liquid aerosol-forming substrate, heating the mesh and the delivered amount of liquid aerosol-forming substrate to a temperature sufficient to volatilize at least a part of the delivered amount of liquid aerosol-forming substrate, by a heater provided outside the tube element. The heater includes an electrical resistive heater.

In an example embodiment, the dispenser is a micropump.

BRIEF DESCRIPTION OF THE DRAWINGS

Features described in relation to one aspect may equally be applied to other aspects of example embodiments.

Example embodiments will now be described, by way of example only, with reference to the accompanying drawings, in which.

DETAILED DESCRIPTION

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In an example embodiment, the mesh is not heated directly by a resistive heater. Instead, the mesh is heated by a surrounding heated tube element. The liquid aerosol-forming substrate is heated indirectly through the heated tube and through the mesh using heat conduction. The mesh improves spreading the liquid aerosol-forming substrate over a heated surface. This enables improved vaporization. As the mesh is heated by heat conduction from the tube element, the surface of the mesh is uniformly heated. Thus, vaporization is further improved. As the liquid is heated in the inner volume of the tube element and is also retained by the mesh, liquid cannot undesirably leak out or drip from the vaporizer. Thus, vaporization of most or even all of the supplied liquid is ensured.

The mesh may be a metal mesh. The mesh may have the shape of a full cylinder. The external diameter of the mesh may be smaller than the inner diameter of the tube element. The mesh may be arranged at the centre of the tube element. The liquid aerosol-forming substrate may spread between the inner surface of the tube segment and the external surface of the mesh. Thus, the liquid aerosol-forming substrate may form a thin hollow liquid cylinder between these two surfaces. The vaporizer may heat this thin hollow liquid cylinder orthogonal on all points of this thin hollow liquid cylinder. The vaporizer may heat orthogonal with respect to the outside and the inside of the thin hollow liquid cylinder. The distance to travel from one side of the liquid layer to the other side may be essentially identical from all points of the thin liquid hollow liquid cylinder. Thus, the heat transfer from the vaporizer to the liquid aerosol-forming substrate may be improved. Contrarily, in the case of a tube segment without a mesh, heat transfers from the outer surface of a full liquid cylinder through the full liquid cylinder. In this configuration, the distance to travel for heat is different depending on the point on the full liquid cylinder where heat applies. Therefore, vaporization is much less uniform and much less effective, particularly at the center of the full liquid cylinder.

The tube element is made from any thermally conductive material. The tube element may be made from aluminium or alumina. The tube element may extend in its longitudinal direction within the range from 10 millimetres to 40 millimetres and may have an outer diameter in the range of 0.5 millimetres to 4.0 millimetres, such as within a range of 1.5 millimetres to 2.5 millimetres. The inner volume of the tube element may have a diameter in the range from 0.3 millimetres to 2.3 millimetres, such as within a range of 1.0 millimetres to 1.6 millimetres.

The mesh may be a metal mesh made from at least one metal material. The metal mesh may be formed by a wire material. The wire material may have a diameter in the range from 0.01 millimetres to 0.04 millimetres, such as in the range from 0.02 millimetres to 0.03 millimetres. The wire material may have a uniform diameter. The mesh may have hole size apertures in the range from 0.01 millimetres to 0.04 millimetres, such as in the range from 0.02 millimetres to 0.03 millimetres. The wire material may for example be stainless steel. The metal mesh may be woven. The metal mesh may have a woven wire mesh pattern. The mesh pattern may be dimensioned in accordance to a surface tension and/or viscosity of the liquid aerosol-forming substrate to obtain a desired (or selected) spreading of the liquid aerosol-forming substrate over the surface of the mesh. The metal mesh improves spreading of the liquid aerosol-forming substrate on the surface of the mesh. The metal mesh is heat conductive. Moreover, the metal mesh is resistant to high heating temperatures. The metal mesh improves heating and vaporization of the liquid aerosol-forming substrate disposed in the inner volume of the tube element. Moreover, the metal mesh is stable over a wide range of heating temperatures. Thus, the average lifetime of the vaporizer is improved.

In an example embodiment, the mesh is a "rolled" mesh. The term rolled means that the mesh is not flat, but that the mesh is curved. The term "rolled" includes the meaning of curved, rolled and rolled up. The rolled mesh may have an opened cross section, e.g. open to an upward direction for a U-shaped rolled mesh. Such a mesh may be arranged in the vaporizer such that for the direction of the opening is the upward direction. The mesh may be curved or rolled around a longitudinal axis or direction of the tube element. The mesh may be curved or rolled around the desired (or selected) flow direction of the liquid aerosol-forming substrate supplied to the inner volume of the tube element. The mesh may be rolled such that two end surfaces of the mesh face or contact each other. The mesh may be rolled-up like a rolled-up carpet. The mesh may be rolled up such that the mesh is layered. The mesh may comprise a first mesh layer and a second mesh layer, wherein the first mesh layer is wrapped around the second mesh layer. The mesh may have an arc-shaped cross section. The mesh may have a cross section of circular, elliptical or helical shape. The cross section may be uniform along the longitudinal direction of the tube element.

In an example embodiment, the mesh extends along a longitudinal direction of the tube element. Thus, the liquid aerosol-forming substrate can be heated uniformly by the tube element and the mesh. Therefore, vaporization is improved.

In an example embodiment, the mesh extends from one end to another end of the tube element. Thus, the liquid aerosol-forming substrate can be spread and heated along the entire length of the tube element. This improves vaporization of the liquid aerosol-forming substrate.

In an example embodiment, the tube element has a free open end. The tube element is configured to receive the liquid aerosol-forming substrate at an end of the tube element opposite to the free open end of the tube element. The free open end may be configured to allow vapor from the liquid aerosol-forming substrate to escape from the inner volume of the tube element. The free open end reduces a flow resistance of the liquid aerosol-forming substrate in the inner volume of the tube element. Thus, spreading of the liquid aerosol-forming substrate in the inner volume towards the free open end is improved.

In an example embodiment, the tube element has a closed free end. The tube element is configured to receive the liquid aerosol-forming substrate at an end of the tube element opposite to the closed free end of the tube element. The tube element having the closed free end further comprises at least one outlet for allowing aerosol to escape from the inner volume of the tube element. The closed end prevents the liquid aerosol-forming substrate from dripping out of the tube element. The tube element comprises a number of micro perforations. The micro perforations are through holes extending from the inner volume to the outer circumferential surface of the tube element. The micro perforations allow escaping of vaporized liquid aerosol-forming substrate from the inner volume of the tube element. Each micro perforation may have a diameter in the range of 50 to 250 micrometers. The micro perforations may be arranged on one or more circumferential rings. The micro perforations may be arranged equally-spaced in circumferential direction, e.g. at 0 degrees and 180 degrees or spanning angles of 45 degrees with respect to each other. The micro perforations may be arranged equally-spaced along the longitudinal direction of the tube element. For a tube element having an open end, the micro perforations may be arranged in a middle section of the longitudinal dimension of the tube element. The micro perforations may be arranged in a section adjacent to the closed free end of the tube element.

In an example embodiment, the tube element is electrically isolated. In particular, the tube element may be electrically isolated from its outer circumferential surface to its inner circumferential surface. This avoids a possible short-circuit between the metal mesh and a metal heater. The tube element may be thermally conductive and electrically non-conductive.

In an example embodiment, the heater comprises an electrical resistive heater. The electric resistive heater may be a metal heater. The electric resistive heater may be a coil heater. The electric resistive heater may be wrapped around the tube element. The electric resistive heater may be partially incorporated in the tube element. The electric resistive heater may extend along the entire or partial longitudinal direction of the tube element.

In an example embodiment, the heater is surrounded or encapsulated by a thermal insulation element. The thermal insulation element may cover the entire heater. This allows to conserve heat energy and to avoid dissipating heat to the surroundings and to other components of an aerosol-generating system besides to the vaporizer.

In an example embodiment, the heater does not extend into the inner volume of the tube element. This allows achieving a uniform temperature distribution within the inner volume. Thus, vaporization is improved. Moreover, a short-circuit between a metal heater and the metal mesh can be avoided. Furthermore, it prevents residues of liquid aerosol-forming substrate adhering at the heater portion from extending into the inner volume.

In an example embodiment, the vaporizer is free of a wicking material. In particular, the inner volume of the tube element is free of wicking material, thereby simplifying its construction.

According to another example embodiment, an aerosol-generating system comprises a vaporizer as discussed above and a delivery unit. The delivery unit is configured to supply a predetermined and/or desired (or selected) amount of the liquid aerosol-forming substrate to the inner volume of the tube element of the vaporizer. The delivery unit may be a micropump. A determined and/or desired (or selected) amount of liquid aerosol-forming substrate is pumped from a liquid storage portion of the aerosol-generating system to the vaporizer. Such a design can allow the production of cartridges without vaporizers. Due to the improved liquid transport, tubing segments and vaporizers may not need to be disposed once the liquid storage portion is empty. By using a pump instead of a passive medium to draw liquid, only the actually required amount of liquid aerosol-forming substrate may be transported to the vaporizer. Liquid aerosol-forming substrate may only be pumped upon demand, for example in response to a negative pressure being applied by an adult vaper.

The micropump may allow on-demand delivery of liquid aerosol-forming substrate at a low flow rate of for example approximately 0.5 to 2 microliters per second for intervals of variable or constant duration. The micropump can be tuned in order to deliver the desired (or selected) amount of liquid aerosol-forming substrate to vaporizer. Consequently, the amount of delivered liquid aerosol-forming substrate can be determined from the amount of pump cycles.

The micropump may be configured to pump liquid aerosol-forming substrates that are characterized by a relatively high viscosity as compared to water. The viscosity of a liquid aerosol-forming substrate may be in the range from about 10 to 500 Millipascalseconds, such as in the range from about 17 to 86 Millipascalseconds.

When adjusting the flow rate, more energy may be required to vaporize the higher amount of delivered liquid aerosol-forming substrate at the vaporizer. Therefore, the temperature settings of the vaporizer may be adjusted in accordance to the liquid flow rate.

The temperature of the heating element may be controlled by electric circuitry. Once a negative pressure has been detected and the heater and/or the tube element of the vaporizer has reached the operating temperature, the electric circuitry may activate the micropump and set a determined flow rate for delivering liquid aerosol-forming substrate to the inner volume of the tube element of the vaporizer for the duration of the negative pressure.

Both the micropump and the heater may be triggered by a negative pressure detection system. Alternatively, the micropump and the heater may be triggered by pressing an on-off button, held for the duration of a negative pressure.

In an example embodiment, the micropump is configured to deliver a determined amount of liquid aerosol-forming substrate from the liquid storage portion to the inner volume of the tube element of the vaporizer upon performing one pump cycle.

As used herein, the terms 'upstream', 'downstream', 'proximal', 'distal', 'front' and 'rear', are used to describe the relative positions of components, or portions of components, of the aerosol-generating system in relation to the direction in which vapor is drawn through an outlet of the system during use thereof.

The aerosol-generating system may comprise an outlet through which in use an aerosol exits the aerosol-generating system and is delivered to an adult vaper. The outlet may also be referred to as the proximal end. In use, an adult vaper applies a negative pressure on the proximal end or outlet of the aerosol-generating system. The aerosol-generating system comprises a distal end opposed to the proximal end or outlet. The proximal end or outlet of the aerosol-generating system may also be referred to as the downstream end and the distal end of the aerosol-generating system may also be referred to as the upstream end. Components, or portions of components, of the aerosol-generating system may be described as being upstream or downstream of one another based on their relative positions between the proximal end, downstream end or outlet and the distal or upstream end of the aerosol-generating system.

In an example embodiment, the aerosol-generating system further comprises a tubing segment through which the liquid aerosol-forming substrate is delivered from the micropump to the vaporizer, and the vaporizer is arranged downstream of an open end of the tubing segment.

In an example embodiment, the aerosol-generating system comprises a main unit and a cartridge. The cartridge may be removably coupled to the main unit, the main unit may comprise a power supply, the liquid storage portion may be provided in the cartridge, and wherein the micropump may be provided in the main unit. In an example embodiment, the main unit further comprises the vaporizer. The main unit may comprise the tubing segment.

The aerosol-generating system according to an example embodiment may further comprise electric circuitry connected to the vaporizer and connected to an electrical power source. The electric circuitry may be configured to monitor the electrical resistance of the vaporizer, and to control the supply of power to the vaporizer dependent on the electrical resistance of the vaporizer.

The electric circuitry may comprise a controller with a microprocessor, which may be a programmable microprocessor. The electric circuitry may comprise further electronic components. The electric circuitry may be configured to regulate a supply of power to the vaporizer. Power may be supplied to the vaporizer continuously following activation of the system or may be supplied intermittently. The power may be supplied to the vaporizer in the form of pulses of electrical current.

The aerosol-generating system comprises a power supply, typically a battery, for example within the main body of the housing. The power supply may be a form of charge storage device such as a capacitor. The power supply may be recharged and may have a capacity that allows for the storage of enough energy for one or more uses; for example, the power supply may have sufficient capacity to allow for the continuous generation of aerosol for a period of around six minutes or for a period that is a multiple of six minutes. In another example, the power supply may have sufficient capacity to allow for a predetermined and/or desired (or selected) number of uses or discrete activations of the heater assembly.

For allowing ambient air to enter the aerosol-generating system, a wall of the housing of the aerosol-generating system, a wall opposite the vaporizer, such as a bottom wall, may be provided with at least one semi-open inlet. The semi-open inlet allows air to enter the aerosol-generating system, but limits/prevents air or liquid from leaving the aerosol-generating system through the semi-open inlet. A semi-open inlet may for example be a semi-permeable membrane, permeable in one direction only for air, but is air- and liquid-tight in the opposite direction. A semi-open inlet may for example also be a one-way valve. In an example embodiment, the semi-open inlets allow air to pass through the inlet only if specific conditions are met, for example a minimum depression in the aerosol-generating system or a volume of air passing through the valve or membrane.

The liquid aerosol-forming substrate is a substrate capable of releasing volatile compounds that can form an aerosol. The volatile compounds may be released by heating the liquid aerosol-forming substrate. The liquid aerosol-forming substrate may comprise plant-based material. The liquid aerosol-forming substrate may comprise tobacco. The liquid aerosol-forming substrate may comprise a tobacco-containing material containing volatile tobacco flavour compounds, which are released from the liquid aerosol-forming substrate upon heating. The liquid aerosol-forming substrate may alternatively comprise a non-tobacco-containing material. The liquid aerosol-forming substrate may comprise homogenised plant-based material. The liquid aerosol-forming substrate may comprise homogenised tobacco material. The liquid aerosol-forming substrate may comprise at least one aerosol-former. The liquid aerosol-forming substrate may comprise other additives and ingredients, such as flavourants.

The aerosol-generating system may be an electrically operated aerosol-generating system. In an example embodiment, the aerosol-generating system is portable. The aerosol-generating system may have a size comparable to a cigar or cigarette. The aerosol-generating system may have a total length between approximately 30 millimetres and approximately 150 millimetres. The aerosol-generating system may have an external diameter between approximately 5 millimetres and approximately 30 millimetres.

According to an example embodiment a method for generating an aerosol comprises the steps of delivering an amount of liquid aerosol-forming substrate to an inner volume of a tube element of a vaporizer, thereby wetting a mesh provided in the inner volume of the tube element with at least a part of the delivered amount of liquid aerosol-forming substrate, heating the mesh and the delivered amount of liquid aerosol-forming substrate to a temperature sufficient to volatilize at least a part of the delivered amount of liquid aerosol-forming substrate, by a heater provided outside the tube element. In an example embodiment, the heater includes an electrical resistive heater.

Figure 1:
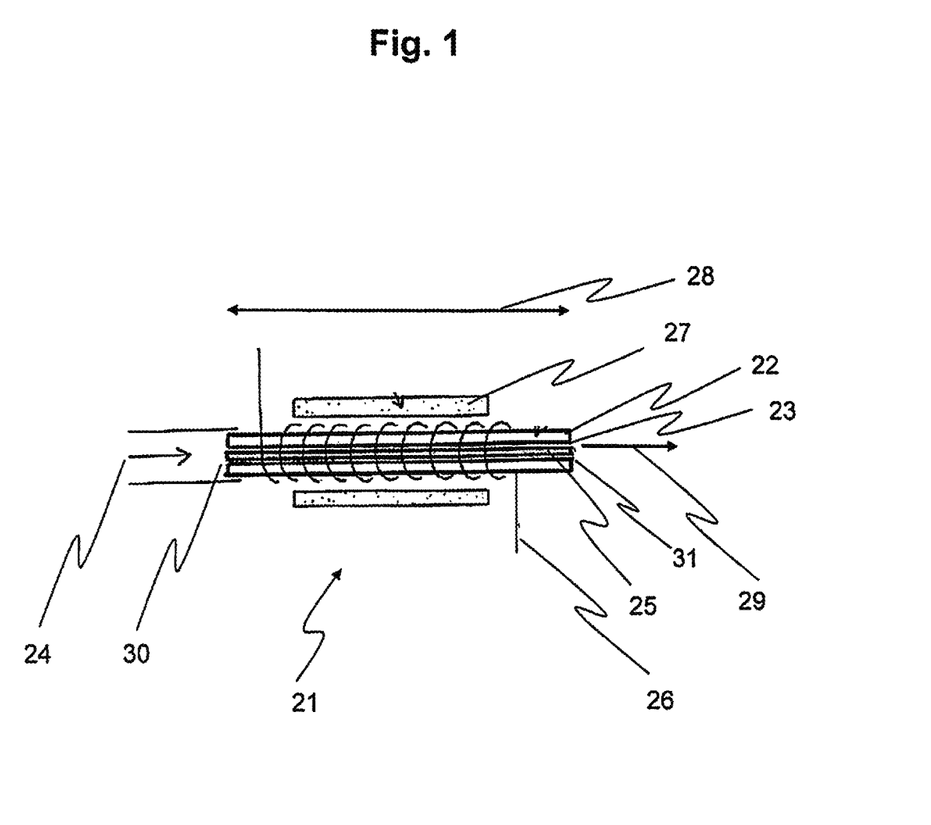
FIG. 1 is a schematic view of a vaporizer in accordance with an example embodiment.

FIG. 1 is a schematic view of a vaporizer in accordance with an example embodiment. The vaporizer 21 comprises a tube element 22, a mesh 25, and a heater 26. The tube element 22 has an inner volume 23 extending in a longitudinal direction 28 of the tube element 22 and the vaporizer 21. The mesh 25 is configured as a rolled metal mesh arranged in the inner volume 23 and extending in the longitudinal direction 28 from one end 30 to the other end 31 of the tube element 22. The external diameter of the mesh 25 is smaller than the diameter of inner volume 23, so that the liquid can spread around the mesh and circulate within the inner volume 23.

A fluid inlet 24 for supplying liquid aerosol-forming substrate to the inner volume 23 is arranged at the one end 30. The other end 31 is configured as an open end for letting escape vaporized liquid aerosol-forming substrate along a direction indicated by arrow 29. The heater 26 is configured as a metal coil which is helically wrapped around the outer circumference of the tube element 22 and along the longitudinal direction 28. A thermal insulation element 27 is wrapped around the heater 26 along the longitudinal direction 28. During operation of the vaporizer, liquid aerosol-forming substrate is supplied via fluid inlet 24 to the inner volume 23 and spreads along the entire mesh 25. An electric current is applied to the heater 26 for heating the tube element 22 and everything in its inner volume 23. The heat of the tube element 22 is conducted to the inner volume 23 and the mesh 25. Thus, the liquid aerosol-forming substrate being spread over the mesh 25 in the inner volume 23 is heated. The liquid aerosol-forming substrate in the inner volume 23 is vaporized and escapes via the other end 31 along arrow 29.

Figure 2A:
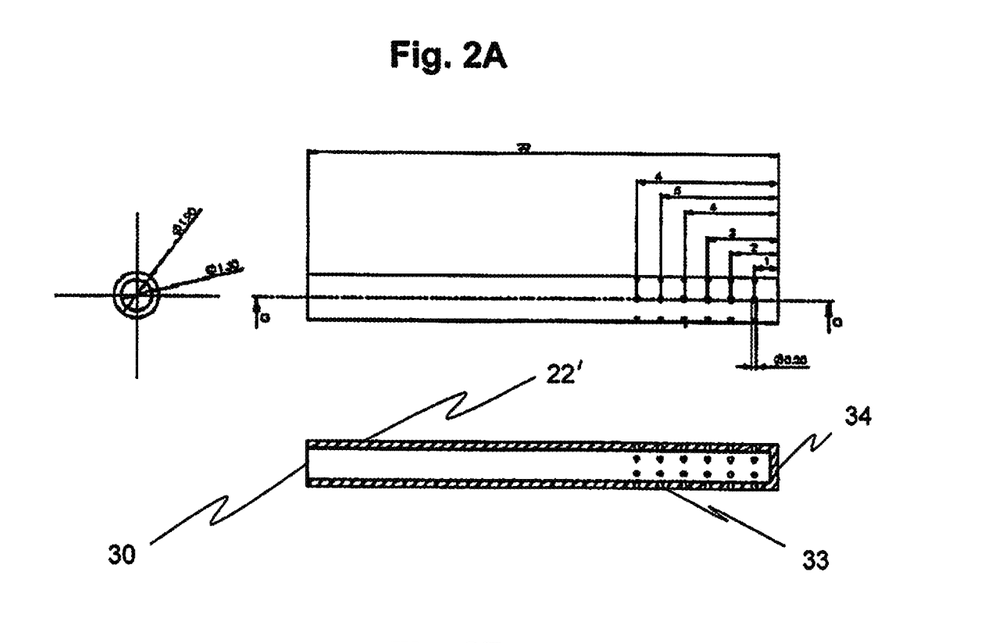
FIG. 2A is a cross section view, side view, and top view of a tube element with a closed end of a vaporizer in accordance with an example embodiment.

FIG. 2A is a cross section view, side view, and top view of a tube element 22' with a closed end of a vaporizer in accordance with an example embodiment. The tube element 22' has a uniform outer diameter of 1.90 millimetres, and the inner volume 23 has a uniform diameter of 1.30 millimetres. The tube element 22' has a length of 20 millimetres in longitudinal direction. An end 34 opposite to end 30 for receiving the liquid aerosol-forming substrate is closed. Six rings of micro perforation holes 33 are arranged 1 to 6 millimetres, respectively, distant from the end 34. Each ring comprises six micro perforation holes 33 of diameter 0.20 millimetres.

Figure 2B:
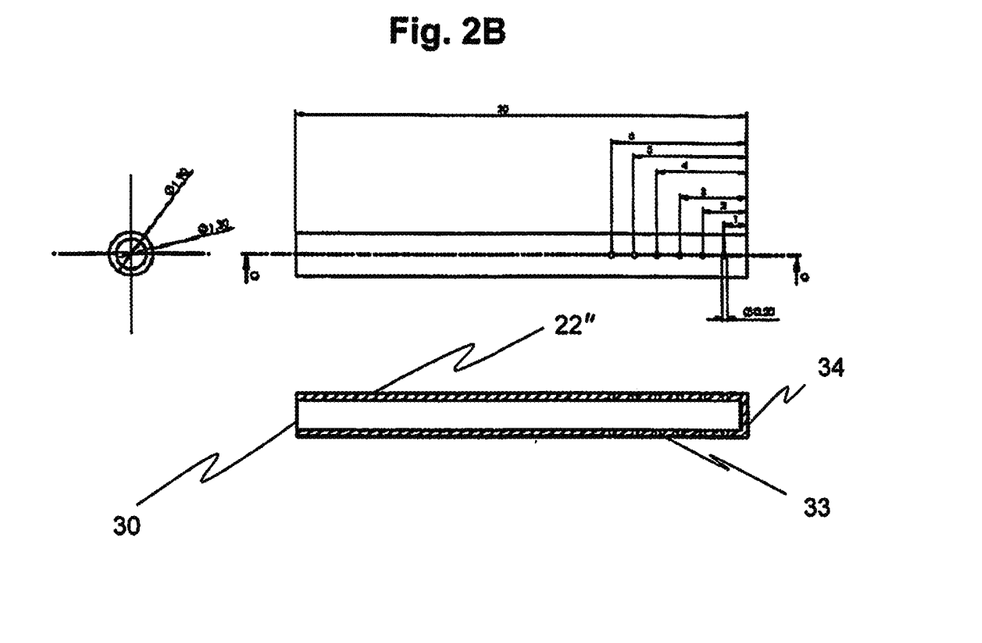
FIG. 2B is a cross section view, side view, and top view of a tube element with a closed end of another vaporizer in accordance with an example embodiment.

FIG. 2B is a cross section view, side view, and top view of a tube element 22" with a closed end of a vaporizer in accordance with an example embodiment. The tube element 22" of FIG. 2B is similar to the one shown in FIG. 2A. The only difference is that each ring of micro perforations only comprises two micro perforation holes arranged at 0 and 180 degrees, respectively.

Figure 3:
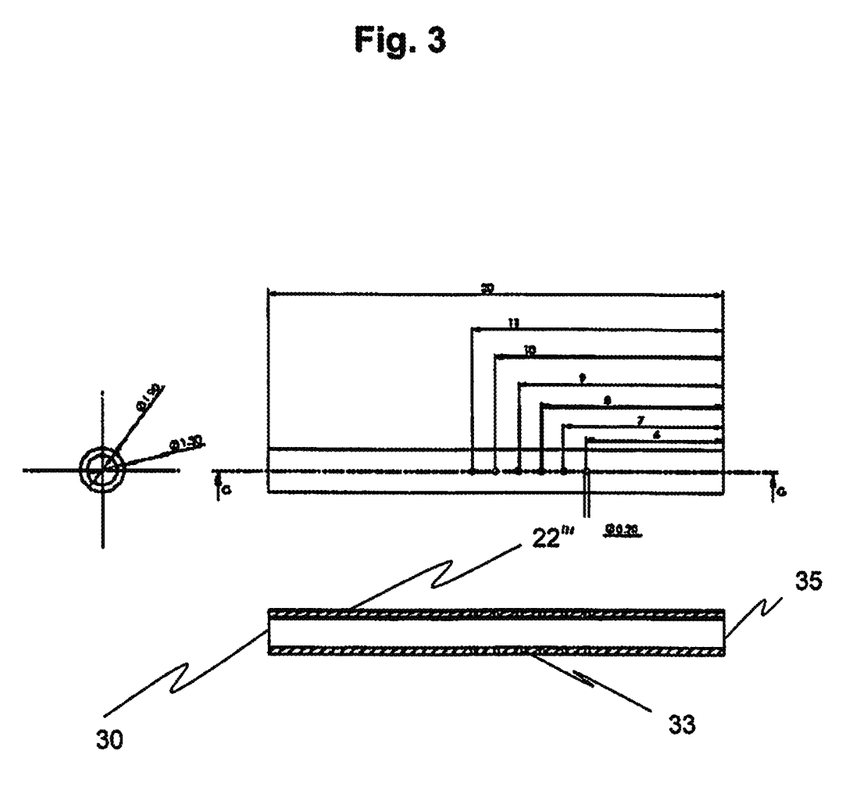
FIG. 3 is a cross section view, side view, and top view of a tube element with an open end of a vaporizer in accordance with an example embodiment.

FIG. 3 is a cross section view, side view, and top view of a tube element with an open end of a vaporizer in accordance with an example embodiment. The dimensions of the tube element 22" shown in FIG. 3 are the same as of FIGS. 2A and 2B. The tube element 22" of FIG. 3 is configured with an open end 35 instead of the closed end 34 of FIGS. 2A and 2B. Six rings of micro perforations with a respective distance of 1 millimetre are arranged in the middle section of the tube element 22". Similar to FIG. 2B, each ring of micro perforations comprises two micro perforation holes arranged at 0 and 180 degrees, respectively.

Figure 4A:
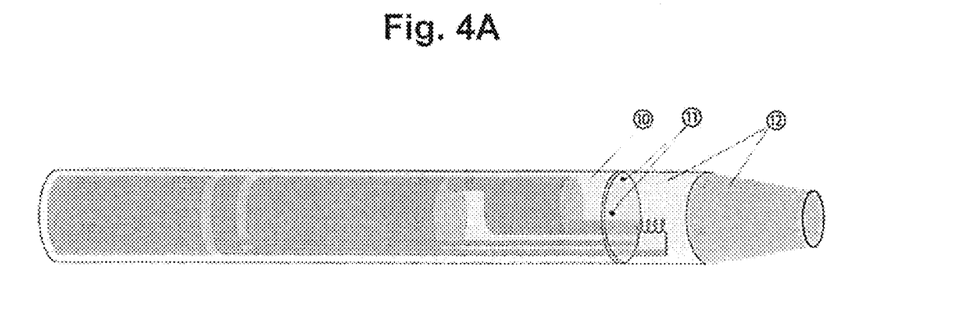
FIG. 4A is a perspective and a topside view of an aerosol-generating system in accordance with an example embodiment.
Figure 4B:
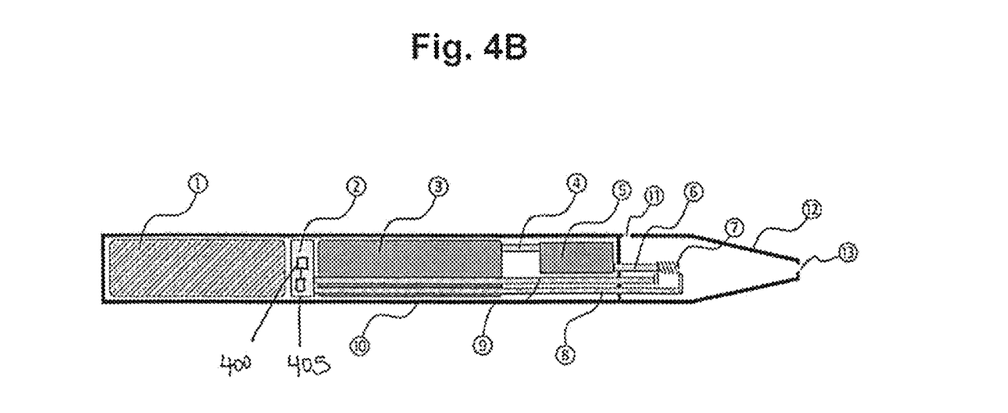
FIG. 4B is a perspective view of an aerosol-generating system in accordance an example embodiment.

FIGS. 4A and 4B are schematic illustrations of an aerosol-generating system. The aerosol-generating system comprises a main unit and a refillable or exchangeable cartridge with a liquid storage portion 3. The main unit comprises a main body 10 and a mouthpiece portion 12. The main body 10 contains a power supply 1, for example a battery such as a lithium iron phosphate battery, electric circuitry 2, a cavity for holding a cartridge, a micropump 5 with an inlet and an outlet, and a vaporizer 7. Electrical connectors 8, 9 are provided at the sides of the main body 10 to provide an electrical connection between the electric circuitry 2, the power supply 1, and the vaporizer 7. Tubing segment 4 is provided to connect an outlet of the liquid storage portion to the inlet of the micropump. Tubing segment 6 leads the flow of liquid aerosol-forming substrate from the outlet of the micropump 5 to the fluid inlet of the vaporizer 7. The mouthpiece portion 12 comprises a plurality of air inlets 11 and an outlet 13. In use, an adult vaper applies a negative pressure on the outlet 13 to draw air from the air inlets 11, through the mouthpiece portion 12 to the outlet 13. Internal baffles are provided to force the air flowing through the mouthpiece portion 12. The vaporizer 7 is configured to heat the liquid aerosol-forming substrate directly after the liquid aerosol-forming substrate exits the tubing segment 6. The vaporizer 7 may be anyone of the vaporizers shown in FIGS. 1-3.

The electric circuitry 2 may include a controller 400 and a memory 405. The controller may be implemented in hardware, a processor configured to execute software, firmware, or any combination thereof, for example. When the controller is hardware, such existing hardware may include one or more Central Processing Units (CPUs), digital signal processors (DSPs), application-specific-integrated-circuits (ASICs), field programmable gate arrays (FPGAs) computers, system on chips (SoCs) or the like configured as special purpose machines to perform the functions of the controller. CPUs, DSPs, ASICs and FPGAs may generally be referred to as processing devices.

In the event where the controller is a processor executing software, the processor is configured as a special purpose machine to execute the software, stored in the memory 405 (e.g., a memory), to perform the functions of the controller. In such an embodiment, the processor may include one or more Central Processing Units (CPUs), digital signal processors (DSPs), application-specific-integrated-circuits (ASICs), field programmable gate arrays (FPGAs) computers, system on chips (SoCs).

The temperature of the heating element may be controlled by electric circuitry 2 (e.g., the controller 400). Once a negative pressure has been detected and the heater and/or the tube element of the vaporizer has reached the operating temperature, the electric circuitry 2 may activate the micropump 5 and set a determined flow rate for delivering liquid aerosol-forming substrate to the inner volume of the tube element of the vaporizer for the duration of the negative pressure.

The electric circuitry 2 (e.g., the controller 400) may be configured to monitor the electrical resistance of the vaporizer 7, and to control the supply of power to the vaporizer 7 dependent on the electrical resistance of the vaporizer 7.

The cartridge is configured to be received in a cavity within the main body 10. In an example embodiment, the cartridge is replaceable, so the adult vaper can exchange it with a new cartridge, when the aerosol-forming substrate provided in the cartridge is depleted. When inserting a new cartridge, a slider at the main body may be moved to expose the cavity. A new cartridge may be inserted into the exposed cavity. The outlet of the liquid storage portion is configured to connect to the inlet of the micropump 5. The main unit is portable and has a size comparable to a cigar or cigarette.

Example embodiments described above illustrate but are not limiting. In view of the above discussed example embodiments, other embodiments consistent with the above example embodiments will now be apparent to one of ordinary skill in the art.

The invention claimed is:

1. A vaporizer for an aerosol-generating system, the vaporizer comprising:
    a tube element defining an inner volume configured to receive an amount of liquid aerosol-forming substrate;
    a mesh in the inner volume of the tube element; and
    a heater, the heater including an electrical resistive heater, and the heater is configured to heat the mesh and the received amount of liquid aerosol-forming substrate to a temperature sufficient to volatilize at least a part of the received amount of liquid aerosol-forming substrate.

2. The vaporizer according to claim 1, wherein the heater is configured to indirectly heat the mesh and the received amount of liquid aerosol-forming substrate by heat conduction via the tube element.

3. The vaporizer according to claim 1, wherein the mesh is a metal mesh.

4. The vaporizer according to claim 1, wherein the mesh is a rolled mesh.

5. The vaporizer according to claim 1, wherein the mesh extends along a longitudinal direction of the tube element.

6. The vaporizer according to claim 1, wherein the mesh extends from one end to another end of the tube element.

7. The vaporizer according to claim 1, wherein the tube element has an open end.

8. The vaporizer according to claim 1, wherein the tube element has a closed end, and the tube element includes a number of micro perforations.

9. The vaporizer according to claim 1, wherein the tube element is electrically isolated.

10. The vaporizer according to claim 1, wherein the heater is surrounded by a thermal insulation element.

11. An aerosol-generating system, comprising:
    a vaporizer including,
        a tube element defining an inner volume for receiving an amount of liquid aerosol-forming substrate,
        a mesh in the inner volume of the tube element, and
        a heater, the heater including an electrical resistive heater, and the heater is configured to heat the mesh and the received amount of liquid aerosol-forming substrate to a temperature sufficient to volatilize at least a part of the received amount of liquid aerosol-forming substrate; and
    a dispenser configured to supply a selected amount of the liquid aerosol-forming substrate to the inner volume of the tube element of the vaporizer.

12. A method for generating an aerosol, the method comprising:
    delivering an amount of liquid aerosol-forming substrate to an inner volume of a tube element of a vaporizer to wet a mesh with at least a part of the delivered amount of liquid aerosol-forming substrate, the mesh being in the inner volume of the tube element; and
    heating the mesh and the delivered amount of liquid aerosol-forming substrate to a temperature sufficient to volatilize at least a part of the delivered amount of liquid aerosol-forming substrate, the heating being performed by a heater provided outside the tube element, the heater including an electrical resistive heater.

13. The aerosol-generating system of claim 11, wherein the dispenser is a micropump.

* * * * *